United States Patent
Hedges et al.

(10) Patent No.: US 10,986,321 B1
(45) Date of Patent: Apr. 20, 2021

(54) METHOD AND DEVICE FOR COLOR CORRECTION OF TWO OR MORE SELF-ILLUMINATED CAMERA SYSTEMS

(71) Applicant: ARTHREX, INC., Naples, FL (US)

(72) Inventors: Benjamin Perry Hedges, Santa Barbara, CA (US); Bruce Laurence Kennedy, Santa Barbara, CA (US); Michael Dominik Steiner, Goleta, CA (US)

(73) Assignee: ARTHREX, INC., Naples, FL (US)

( * ) Notice: Subject to any disclaimer, the term of this patent is extended or adjusted under 35 U.S.C. 154(b) by 0 days.

(21) Appl. No.: 16/708,892

(22) Filed: Dec. 10, 2019

(51) Int. Cl.
| | |
|---|---|
| *H04N 9/73* | (2006.01) |
| *H04N 5/225* | (2006.01) |
| *H04N 9/64* | (2006.01) |
| *G06T 7/90* | (2017.01) |
| *G06T 7/80* | (2017.01) |
| *H04N 9/77* | (2006.01) |
| *H04N 7/01* | (2006.01) |
| *A61B 1/00* | (2006.01) |
| *A61B 1/045* | (2006.01) |
| *H04N 5/247* | (2006.01) |

(52) U.S. Cl.
CPC ............. *H04N 9/73* (2013.01); *A61B 1/0002* (2013.01); *A61B 1/00045* (2013.01); *A61B 1/045* (2013.01); *G06T 7/80* (2017.01); *G06T 7/90* (2017.01); *H04N 5/2256* (2013.01); *H04N 5/247* (2013.01); *H04N 7/0127* (2013.01); *H04N 9/646* (2013.01); *H04N 9/77* (2013.01); *G06T 2207/10016* (2013.01); *G06T 2207/10024* (2013.01); *G06T 2207/10068* (2013.01); *H04N 2005/2255* (2013.01)

(58) Field of Classification Search
CPC combination set(s) only.
See application file for complete search history.

(56) References Cited

U.S. PATENT DOCUMENTS

| | | | |
|---|---|---|---|
| 2009/0105543 A1* | 4/2009 | Miller ................. | A61B 1/122 600/155 |
| 2014/0184765 A1* | 7/2014 | King ................ | A61B 1/00057 348/65 |
| 2016/0058514 A1* | 3/2016 | Ogawa ................ | A61B 34/74 600/104 |

(Continued)

*Primary Examiner* — Jefferey F Harold
*Assistant Examiner* — Humam M Satti
(74) *Attorney, Agent, or Firm* — Karish & Bjorgum, PC

(57) ABSTRACT

A device and method for color correction of two camera systems each having an imaging device and an illumination source. The camera systems are separately white balanced with the imaging device outside a scene. Their white balance gains and color correction matrices are saved. Based on the measurements, combined white balance gains and combined color correction matrices are computed and saved. Thereafter, with the imaging devices in a scene, performing white balancing by measuring the R, G, and B values of both imaging devices together, and then white balancing by measuring the R, G, and B values of each separate imaging device with the other camera system's light off. Comparisons are made of each camera's scene measurements against the combined scene measurements. If they are significantly different, the combined light set of white balance gain and color correction matrix is applied to digital signal processing paths of each camera system.

15 Claims, 5 Drawing Sheets

(56) References Cited

U.S. PATENT DOCUMENTS

| | | | |
|---|---|---|---|
| 2017/0112354 A1* | 4/2017 | DiCarlo | H04N 9/04 |
| 2018/0214015 A1* | 8/2018 | Calabrese | A61B 1/018 |
| 2018/0220052 A1* | 8/2018 | Granneman | A61B 1/00009 |
| 2020/0104998 A1* | 4/2020 | Dacosta | A61B 5/0071 |

* cited by examiner

METHOD AND DEVICE FOR COLOR CORRECTION OF TWO OR MORE SELF-ILLUMINATED CAMERA SYSTEMS

FIELD OF THE INVENTION

The invention relates to methods, systems and devices for imaging structures using endoscopic camera systems, and more particularly to a method and device that provides color correction of two or more self-illuminated camera systems.

BACKGROUND OF THE INVENTION

Endoscopic medical instruments (also referred to herein as "endoscopes") including endoscopic camera systems provide surgeons with a view of an area of a medical patient's body being worked on during endoscopic procedures without the necessity of fully opening the area, thereby facilitating less-invasive surgical procedures. In endoscopic surgeries, illumination is typically directed into very small and tight closed cavities and spaces in the body. Such illuminating lighting can be provided by fiber optics or other light channels that carry the light from a distant light source. The illumination source, e.g., LEDs, can also be located onboard the endoscope and be focused directly out of the endoscope. Some endoscopes use light channels (e.g., optical fibers or translucent plastic light tubes) to direct the light from onboard LEDs to points outside the endoscope. The illumination sources can also be one or a mix of xenon, halogen, LED and laser light.

The surgical field in endoscopic procedures can present unique lighting and imaging challenges. When using camera systems to view an object under lighting, there are often unrealistic color casts in the image that can make it difficult to visualize the field of surgery. This is particularly true in the tight confines of endoscopic surgery where the distances between the light sources and the tissue being illuminated can vary, and where the reflected light can be affected by the color of the tissue being illuminated and the shadows that are cast.

White balancing (WB) is the process of removing unrealistic color casts, performing color correction, and establishing color fidelity so that objects which appear white in person are rendered white in a photograph or a visual display, such as a computer screen. This is important because medical practitioners often rely on color when making diagnostic and other medical decisions. Proper camera white balance has to consider the color temperature of a light source. The color temperature refers to the relative warmth or coolness of white light. While the human eye is good at judging what is white under different light sources, digital cameras can have great difficulty with auto white balance (AWB), and thus unsightly blue, orange, or even green color casts can result, which can interfere with optimal use of an endoscope.

Endoscopic camera systems may include two or more cameras and light sources arranged at different angles so that the field of view can be enlarged (e.g., by stitching together images from different cameras) and/or so that different views can be seen without having to reposition one endoscope. Unlike single camera systems, when dealing with multiple camera endoscopes, the process of white balancing becomes more complicated. When a white balanced self-illuminated camera system (CS2) is used as a secondary (or tertiary, quaternary, etc.) view to another white balanced self-illuminated camera system (CS1) the scene is now illuminated by two (or more) independent light sources. The color temperature of the scene illumination (CS1 &2) will change depending on each system's location in the scene and intensity of each system's illumination. The color temperature can also be affected depending on what tissue/structures (e.g., white vs. red tissue) are being illuminated by a particular light source, the distances between the camera lenses and the tissue being illuminated, and the type of light source used. This change in scene illumination color temperature may cause erroneous color reproduction in one or more camera systems involved.

Current systems of white balancing multiple endoscopic camera systems rely on white balancing each of the multiple cameras consecutively against a white background before beginning a procedure. These prior art systems do not accomplish white balance after a procedure has begun and indeed, if white balancing is accidently attempted, the endoscope usually must be removed and its white balance recalibrated.

Therefore, there remains a need for a system to correct color reproduction errors inherent in systems with multiple self-illuminated cameras.

SUMMARY OF THE INVENTION

The present invention provides a color correction system for at least two self-illuminated endoscopic camera systems, the color correction system comprising a central processing unit; an input/output interface for camera control units; and a memory for retention of collected data and operating software or firmware for the color correction system; wherein each of the at least two self-illuminated endoscopic cameras comprises an imaging device and an illumination source.

In another embodiment the invention provides a device for color correction of at least two self-illuminated endoscopic camera systems, each self-illuminated endoscopic camera system having at least one imaging device and one illumination source, the device for color correction computing and saving white balancing information and color correction matrices for each of the at least two self-illuminated endoscopic camera systems, and the device further computing and saving combined white balancing information and color correction matrices for the at least two self-illuminated endoscopic camera systems; and comprising: a central processing unit; an input/output interface for camera control units; a memory for retention of collected data and operating software or firmware for the device for color correction; and a control to control operation of the color correction device.

In yet another embodiment, the invention provides a device for color correction of at least two self-illuminated endoscopic camera systems, each self-illuminated endoscopic camera system having at least one imaging device and one illumination source, the device comprising: a central processing unit; an input/output interface for camera control units; a memory for retention of collected data and operating software or firmware for the device for color correction; and a control to control operation of the color correction device; wherein when the color correction device is activated, white balancing of the at least two self-illuminated endoscopic camera systems takes place with the at least two self-illuminated endoscopic camera systems outside of a scene, and then with the two self-illuminated endoscopic camera systems placed in and used simultaneously in the scene.

The invention further provides a method for color correction of at least two self-illuminated endoscopic camera systems, each self-illuminated endoscopic camera system having at least one imaging device and one illumination light, the method comprising the following steps: (A) with the imaging devices oriented outside of a scene; measuring and saving white balancing information and color correction matrices for each of the at least two self-illuminated endoscopic camera systems; and computing and saving combined white balancing information and color correction matrices for the at least two self-illuminated endoscopic camera systems; and (B) with the at least two imaging devices positioned in a scene; with the illumination sources of the at least two self-illuminated endoscopic cameras turned on, measuring and saving in the memory separate values of R (red), G (green), and B (blue) for each of at least two self-illuminated endoscopic camera systems as a combined scene; with the illumination source of one of the at least two endoscopic camera systems turned on and the illumination source of the other of the at least two endoscopic camera systems turned off measuring and saving in the memory average values of R (red), G (green), and B (blue) for the endoscopic camera systems with the illumination source on, and repeating this measuring and saving step except with the illumination source of the other of the least two endoscopic camera systems switched from off to on and the illumination source of the original endoscopic camera systems switched from on to off, and carrying out comparisons of the scene measurements of the at least two endoscopic camera systems when turned on against the combined scene measures and if necessary, making corrections to the white balance of the endoscopic camera systems.

In yet a further embodiment, the invention provides a method for color correction of at least two self-illuminated endoscopic camera systems, each self-illuminated endoscopic camera system having an imaging device, an illumination light, and a camera control unit, the method comprising the following steps: with the at least two imaging devices oriented outside of a scene; (a) white balancing the at least two self-illuminated camera systems to determine white balance gains for each of the at least two self-illuminated camera systems and saving the white balance gains in a memory along with color correction matrices for each of the at least two self-illuminated camera systems; and (b) based on each of the individual white balance gains and color correction matrices, computing combined white balance gains and an accompanying set of combined color correction matrices, and saving the combined white balance gains and the accompanying set of combined color correction matrices in the memory; and with the at least two imaging devices positioned in a scene; (c) with illumination of the at least two endoscopic camera systems turned on, separately measure average values of R (red), G (green), and B (blue) within a predetermined window of a captured scene for each of the at least two endoscopic camera systems and save in memory as a combined scene measurements; (d) with illumination of a first one of the at least two endoscopic camera systems turned on and the second of the at least two endoscopic camera systems turned off, measuring the average values of R, G, and B within the predetermined window of the captured scene for the one of the at least two endoscopic camera systems and saving average values of R, G, and B of the first one of the at least two endoscopic camera systems in memory as a first scene measurements; (e) with illumination of the second one of the at least two endoscopic camera systems turned on and the first one of the at least two endoscopic camera systems turned off, measuring the average values of R, G, and B within the predetermined window of the captured scene for the second one of the at least two endoscopic camera systems and saving average values of R, G, and B of the second one of the at least two endoscopic camera systems in memory as a second scene measurements; (f) carrying out a first comparison between the first scene measurements and the combined scene measurements, and if the first scene measurements is significantly different as perceived through close observation than the combined scene measurements, then applying the combined-light set of white balance gain and the color correction matrix to a digital signal processing path of the first one of the at least two endoscopic camera systems; (g) carrying out a second comparison between the second scene measurements and the combined scene measurements, and if the second scene measurements is significantly different as perceived through close observation than the combined scene measurements, then applying the combined-light set of white balance gain and the color correction matrix to a digital signal processing path of the second one of the at least two endoscopic camera systems; and (h) repeating steps (f) and (g) as needed to correct the color balance of at least two self-illuminated endoscopic camera systems.

In still another embodiment, the invention provides a method for color correction of at least two self-illuminated endoscopic camera systems, each self-illuminated endoscopic camera system having at least one imaging device and one illumination light, the method comprising the following steps: (a) the camera systems are first separately white balanced outside of a scene and their white balance gains and color correction matrices are saved; (b) based on the measurements, combined white balance gains and combined color correction matrices are computed and saved; and (c) with the two camera systems in a scene, performing white balancing by measuring the R, G, and B values of both cameras together, and then white balancing by measuring the R, G, and B values of each separate imaging device with the other camera system's light off; and (d) comparing each imaging device's scene measurements against the combined scene measurements and if they are significantly different, the combined light set of white balance gain and color correction matrix is applied to digital signal processing paths of each camera system.

These and other features of the invention are described below.

DETAILED DESCRIPTION

Given the above described limitations on the white balancing of multiple camera endoscopes, the inventors have developed a system that addresses these shortcomings.

Figure 1:
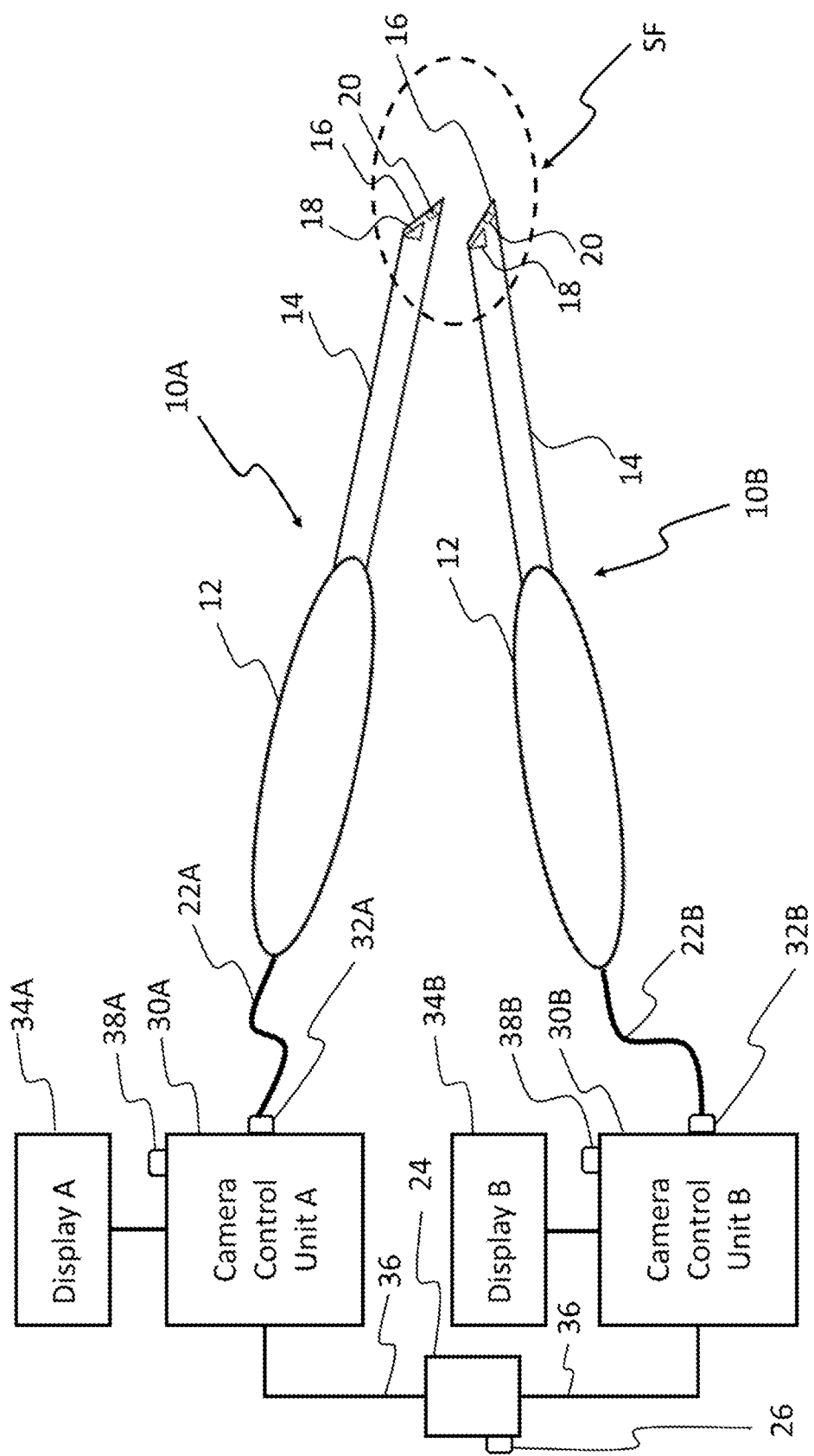
FIG. 1 is a diagram depicting two endoscope camera systems with their tips pointed in an overlapping surgical field of view, with the two endoscope camera systems connected to two separate camera control units.

Turning first to FIG. 1, there is shown a diagrammatic view showing a first exemplary arrangement of two separate endoscopic camera systems 10A and 10B (with "endoscopic camera systems" sometimes referred to herein as "endoscopes"). Each endoscopic camera system 10A and 10B typically comprises a handle 12 and an endoscope 14 extending therefrom, with each endoscope 14 having a distal end 16. An imaging device 18 (for example a charge coupled device (CCD)) may be located at the distal end 16. The imaging device may also include optics and an electromechanical assembly. Alternatively the imaging device 18 can be located, for example, in the handle 12, or even outside of the endoscopic camera system, with an image guide being used to transmit images being viewed to the imaging device 18 (not shown). At least one illumination light source 20, for example a LED light, can be positioned at the distal end 16 of the endoscope 14. Alternatively, an illumination light source 20 can be placed distant to the distal end 16, with the light being transmitted out the distal end via a connection light tube (not shown). Alternatively, an illumination light source 20 for a camera system can be located elsewhere and the light transmitted to a surgical site.

As further shown in FIG. 1, each handle 12 is connected with data and power cables 22A and 22B to Camera Control Unit A 30A and Camera Control Unit B 30B via input plugs 32A and 32B, respectively. The endoscopes can be laparoscopes, arthroscopes, etc. If either or both of the endoscopic camera systems 10A and 10B are wireless devices then instead of physical data and power cables 22A and 22B there are wireless data links (not shown) between the handle 12 and the Camera Control Units 30A and 30B. As will be understood by those of skill in the art based on this disclosure, three or more endoscopic camera systems may also be used together. However, for the balance of the discussion, a two endoscope system is described.

The Camera Control Unit A 30A and Camera Control Unit B 30B are connectable to display A 34A and display B 34 B, respectively to display images from their respective endoscopic camera systems 10A and 10B. For the convenience of the user, in certain situations, it is possible that Camera Control Unit A 30A and/or Camera Control Unit B 30B can be made to display a composite image of the scene being viewed on one or more of Display A 34A or Display B 34B. Alternately, a single display with split screen capabilities (not shown) can be used instead of Display A 34A and Display B 34B.

In FIG. 1, the two endoscopes 14 of the two endoscopic camera systems 10A and 10B are shown placed in a surgical field SF and their corresponding illumination light sources 20, when turned on at the same time, illuminate the surgical field SF and impact the total light color, intensity, and quality in the surgical field SF. While the term surgical field is used herein, this term can refer to any location or "scene" where the two or more endoscopic camera systems 10A and 10B are being used. While the illumination light source 20 is shown as being roughly on a same plane as imaging device 18 at the distal tip 16, if desired, the illumination light source 20 could be located to aim its light not directly in the field of view of the imaging device 18. The light sources 20 in the endoscopic camera systems 10A and 10B can have the same or different desired lighting characteristics, such as light frequency including light color, intensity, illumination focus (e.g., narrow spotlight versus wide spread light) and direction.

Overall, the at least two endoscopic camera systems 10A and 10B can be identical, or can be different in design and operation, including their make, model, and type of camera and number and characteristics of their light sources. Thus, when operated, image data collected by the endoscopic camera systems 10A and 10B will be transmitted via data/power cables 22A and 22B to Camera Control Unit A 30A and Camera Control Unit B 30B, respectively. Camera Control Unit A 30A and Camera Control Unit B 30B can be interconnected via a data link 36 which links Camera Control Unit A 30A and Camera Control Unit B 30B through a color correction unit 24 which can correlate data collected by the two endoscopic camera systems 10A and 10B and their respective connected Control Unit A 30A and Camera Control Unit B 30B and which can include hardware, firmware, and software needed to carry out the color correction system of the invention. Alternatively, the camera control units may be connected to each other with one of the camera control units containing the color correction unit 24.

Each Control Unit A 30A and Camera Control Unit B 30B can optionally include a white balance reset and correction button 38A and 38B, respectively, to allow for manual resetting and correction of the white balance by an operator. Alternately, a white balance reset and color correction button 26 can be included with the color correction unit 24. As an alternative to there being a dedicated color correction unit 24, a general purpose computer loaded with software can instead be connected to the Camera Control Units 30A and 30B and used to carry out the steps of the invention as described further below. In the case of a general purpose computer, there would not be separate and dedicated white balance reset and color correction buttons 26, 38A or 38B as such computer program could include a predetermined keypad button to click or a software icon to select.

Furthermore, the system of the invention can be set up such that initial white balancing of the two or more endoscopes 10A and 10B, before the endoscopes are inserted into a surgical field, can be activated by initiation of a computer program in either a dedicated color correction unit 24 or a general purpose computer. Thereafter, with the endoscopes placed in the surgical field, color correction steps can take place automatically and without the need for an operator to push any buttons, for example, if the system detects that one or more of the endoscopes 10A and/or 10B has been moved or the lighting conditions in the surgical field have changed. Further details on the operation of the white balance resetting process will be discussed further below.

Figure 2:
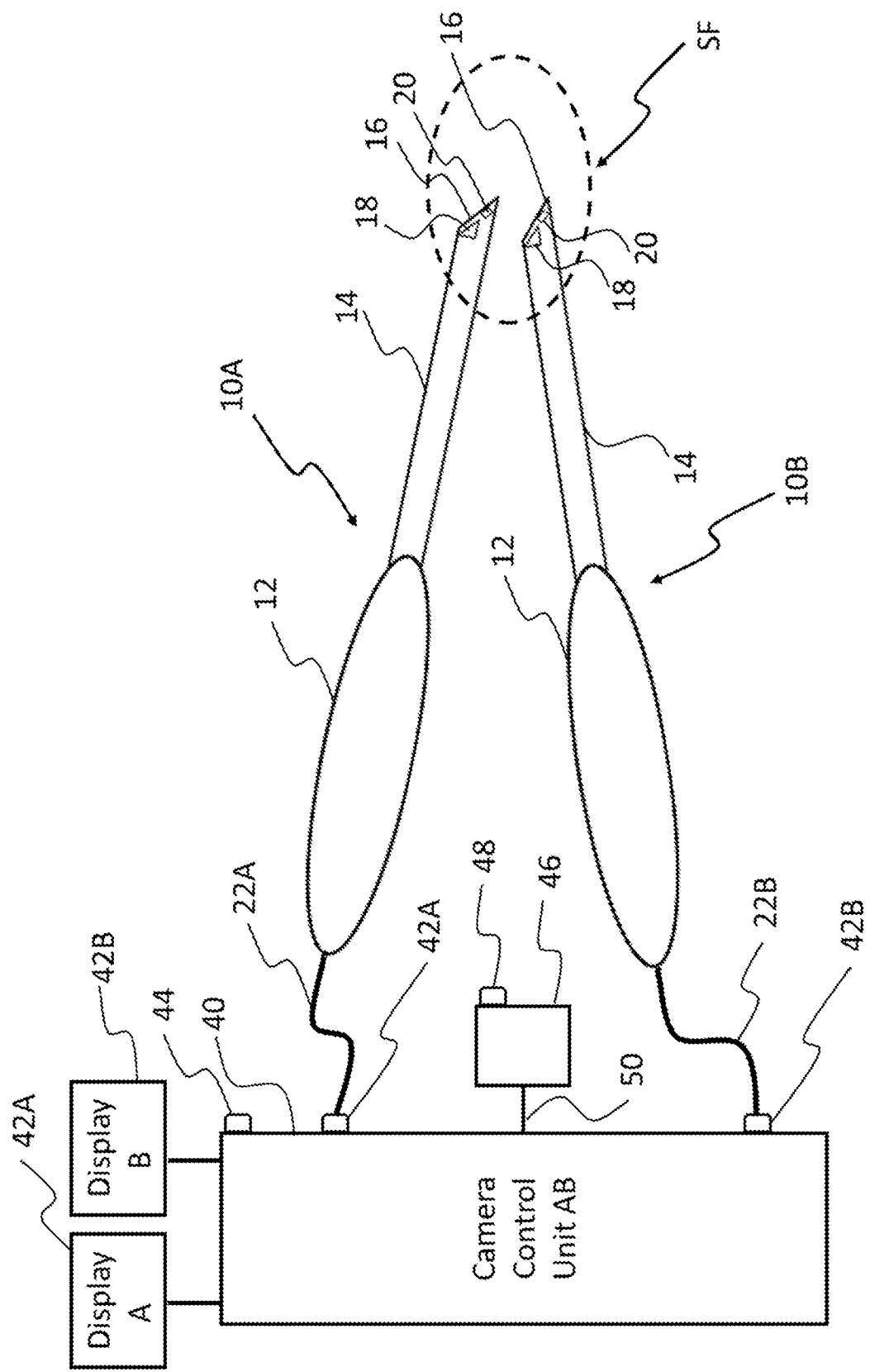
FIG. 2 is a diagram depicting two endoscope camera systems with their tips in an overlapping surgical field of view, with the two endoscope camera systems connected to a single camera control unit.

Turning to FIG. 2, there is shown a variation on the first exemplary arrangement of two separate endoscopic camera systems 10A and 10B, where instead of each endoscopic camera system 10A and 10B being connected to its own dedicated Camera Control Unit A 30A and Camera Control Unit B 30B, respectively, as in the case of the setup of FIG. 1, the at least two endoscopic camera system 10A and 10B (as described with reference to FIG. 1) are connected to a single Camera Control Unit AB 40. The Camera Control Unit AB 40 can be connectable to two displays (Display A 42A and Display B 42B), or alternatively, a single display with split screen capabilities (not shown) can be used instead of two dedicated display (Display A 42A and Display B 42B). If either or both of the endoscopic camera systems 10A and 10B are wireless devices then instead of physical data and power cables 22A and 22B there are data links (not shown.)

The Camera Control Unit AB 40 can optionally be equipped with a white balance reset and correction button 44 to allow for manual resetting and correction of the white balance of the endoscopic camera system 10A and 10B by an operator. A color correction unit 46 can be interconnected to the Camera Control Unit AB 40 via a data link 50 and correlate data collected by the two endoscopic camera systems 10A and 10B and can include hardware, firmware and/or software needed to carry out the color correction process of the invention. A white balance reset and color correction button 48 can be included with the color correction unit 46 to obviate need for a white balance reset and correction button 44 on the Camera Control Unit AB 40.

As with the arrangement of FIG. 1, as an alternative to a dedicated color correction unit 46, a general purpose computer loaded with software can instead be connected to the Camera Control Unit 40 and used to carry out the steps of the invention as described further below. If this the case, then there would not be separate white balance reset and color correction buttons 44 or 48 as such computer program could include a predetermined keypad button to click or a software icon to select.

Furthermore, the system of the invention can be set up such that initial white balancing of the two or more endoscopes 10A and 10B before the endoscopes are inserted into a surgical field can be activated by initiation of a computer program in either a dedicated color correction unit 46 or a general purpose computer. Thereafter, with the endoscopes placed in the surgical field, color correction steps can take place automatically and without the need for an operator to push any buttons, for example, if the system detects that one or more of the endoscopes 10A and/or 10B has been moved or the lighting conditions in the surgical field has changed. Further details on the operation of the white balance correction process will be discussed further below.

Figure 3:
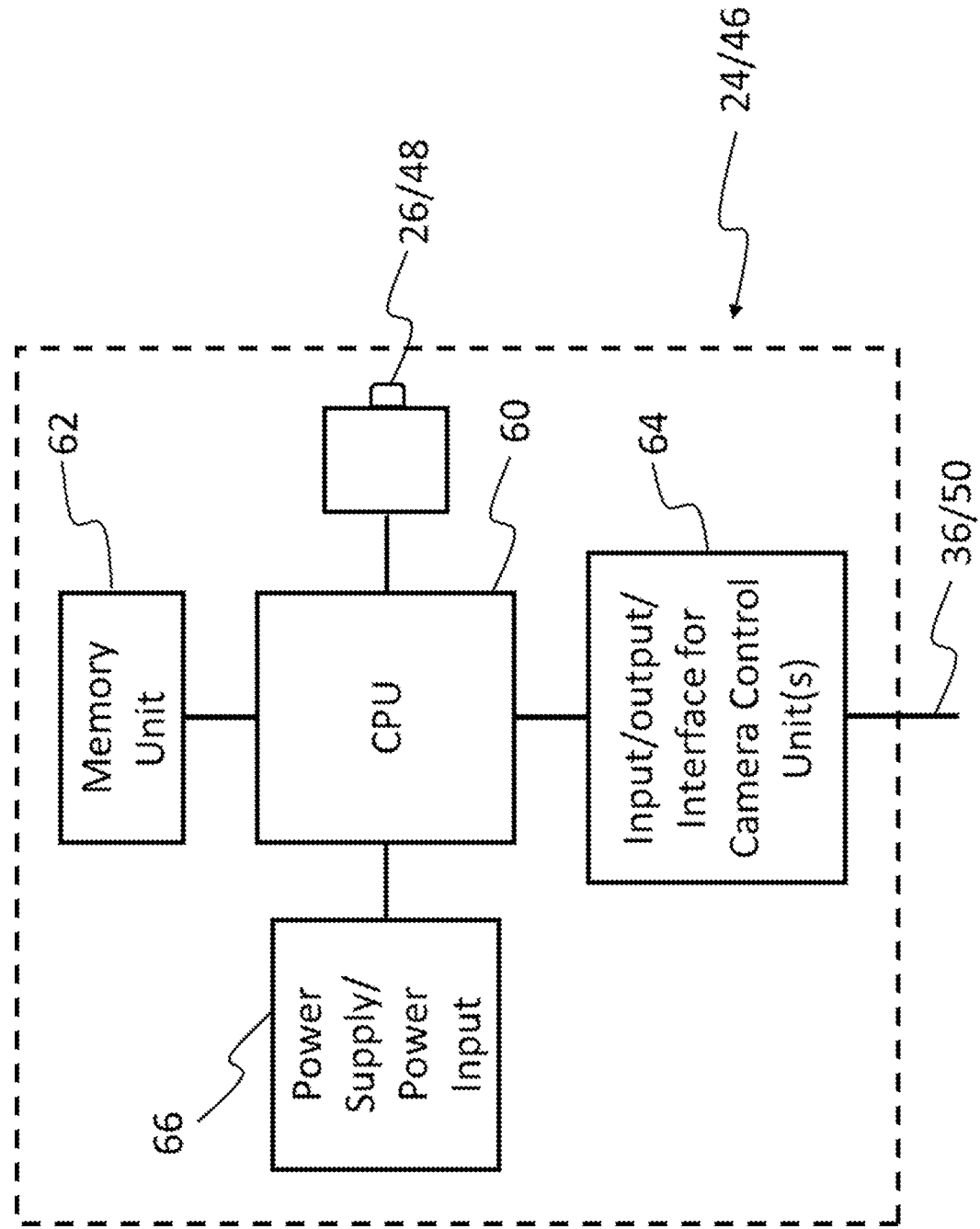
FIG. 3 is an exemplary block diagram showing an exemplary embodiment of parts of a color correction system of the invention.

Having described the layout of the typical physical hardware for endoscopy including the endoscopic camera systems, camera control units, displays, and their interconnections, we now turn to a description of an exemplary embodiment of the color balance error correction system of the invention. FIG. 3 is an exemplary block diagram showing an exemplary embodiment of a color correction unit 24/46 of the invention. The color correction unit 24/46 includes a CPU 60, memory 62, an input/output interface for the camera control unit(s) 64 with a data link 36/50, a power supply/power input 66, and white balance reset and color correction button 26/48 to initiate the process as will be described further below. As noted above, in lieu of a dedicated color correction unit 24/46, the functions and operations of a color correction unit 24/46 can be replicated in a general purpose computer that can be connected to the endoscopes 10A and 10B and/or to the Camera Control Unit(s).

As described above, the color balance error correction system of the invention can reside in a separate module or unit, such as the color correction units 24/46 described above in FIGS. 1 and 2. The possibility of replicating the functionality in a general purpose computer was also discussed above. Another possibility is to integrate the required features of the color correction unit directly into one or more of the Camera Control Unit A 30A, Camera Control Unit B 30B, or Camera Control Unit AB 40. So long as the functionality is provided, the hardware, firmware, and software can reside anywhere in a setup.

Thus, regardless of the physical location of the necessary electronics, firmware, and/or software in a setup, the following steps are followed in the invention to correct color balance errors when using two or more endoscopic camera systems with their lights switched on at the same time during an endoscopic procedure. The imaging devices can be located at the distal end of the endoscope, e.g., camera chip on tip, can be located in the proximal end of the endoscope, or can be located in other locations as desired. Furthermore, the imaging devices can be reusable or disposable. The camera systems can function such that one camera system functions as a master device and the other camera system functions as a slave device. Lastly, the illumination of either camera system can be disabled or interleaved with frames of another camera system.

Figure 4:
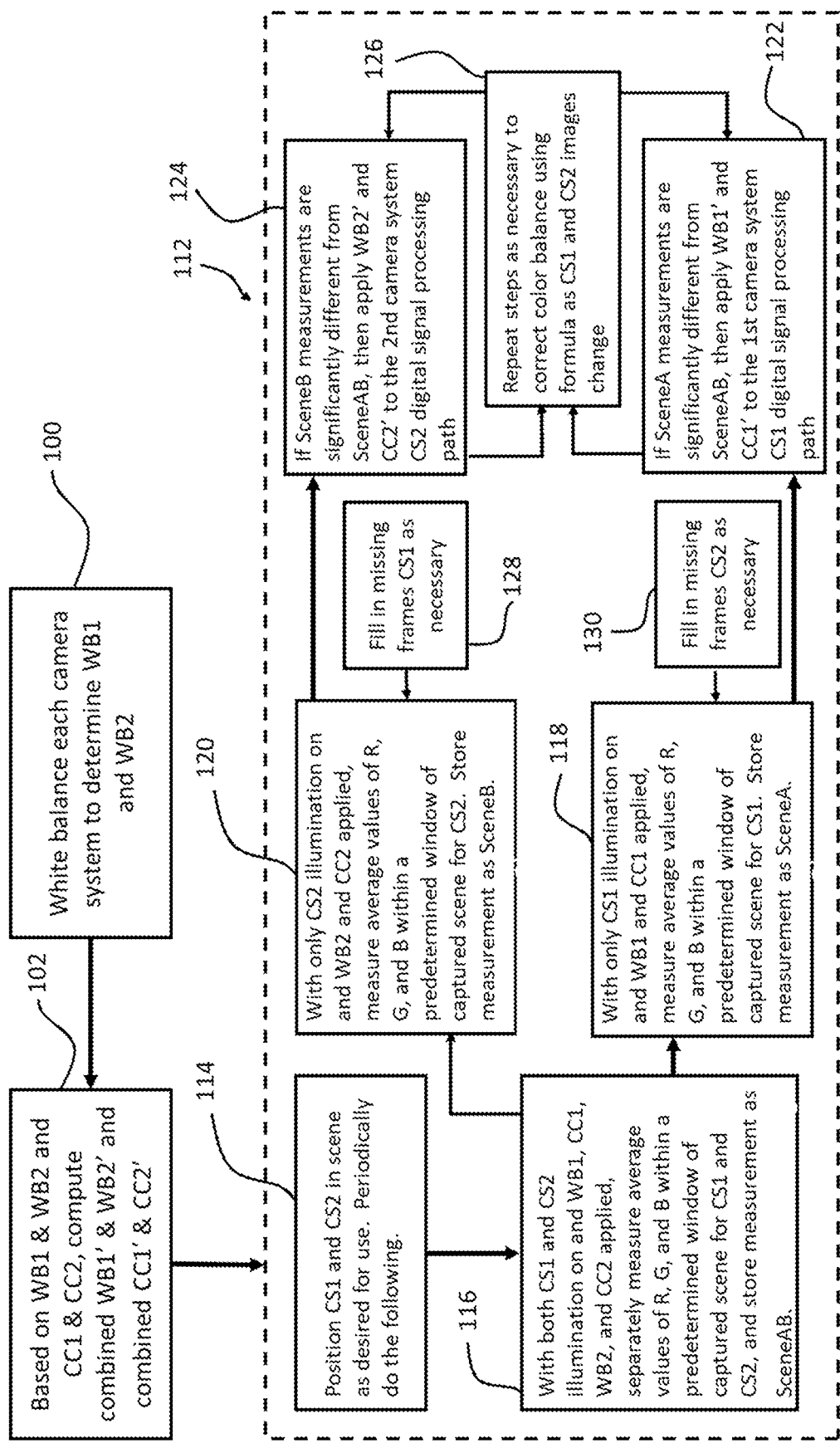
FIG. 4 is a flow chart showing an exemplary embodiment of a method of color correction of two or more self-illuminated camera systems of the invention.

FIG. 4 a flow chart showing an exemplary embodiment of a method and system of color correction of two or more self-illuminated camera systems of the invention.

In the first step 100 of the method and system on the flowchart, white balancing is preformed as usual for each camera system using its respective light source. In an embodiment, this is accomplished with the imaging devices of endoscopic camera systems A and B outside of a surgical field and pointed at a section of pure white material, for example, such as a piece of pure white card stock or a piece of white gauze. The camera systems are cycled on and the individual white balance gains, WB1 and WB2, are stored in separate white balance gain memories for each individual digital signal processing path for each camera. Each signal processing path has its own color correction matrix as well, CC1 and CC2, respectively, which are also stored in memory along with WB1 and WB2, for example in the memory unit 62 of the color correction unit 24/46 of FIG. 3. As noted above, in lieu of having a dedicated color correction unit, the functionality and steps of the invention can be carried out by a general purpose computer which is connected to the Camera Control Unit(s) or can even be carried out in the Camera Control Unit(s). However, for sake of discussion of this embodiment of the steps and method, it will be assumed that there is a dedicated color correction unit present.

Next, in step 102, based on the individual white balance gains WB1 and WB2 and the individual color correction matrixes CC1 and CC2 for each camera determined from the step 100, compute a combined-light set of white balance gains WB1' and WB2', and an accompanying set of combined-light set of color correction matrixes CC1' and CC2'. The computation of WB1' and WB2' and CC1' and CC2' values can be computed by the color correction unit 24/46 and stored therein in its memory unit 62.

The next group of steps occur with the endoscopic camera systems 10A and 10B situated in a body (in a surgical field SF) or "scene" during a procedure and are generally shown in the steps of block 112 of FIG. 4. In step 114, the camera system 1 (CS1) and the camera system 2 (CS2) (which can correspond to the endoscopic camera systems 10A and 10B, respectively, as shown in FIGS. 1 and 2) are physically positioned in the body location (the surgical field SF), as desired for use. In the system of the invention the following steps periodically take place. The periodicity of the steps can be at predetermined intervals, or the periodicity can be triggered or increased whenever movement is detected in one or more of the endo scopes or in some other manner. The exemplary formulas used in this process are discussed further below.

In step 116, with both CS1 and CS2 light sources turned on (e.g., the illumination light sources 20 in each endoscopic camera systems 10A and 10B), the system separately measures the average values of R (red), G (green), and B (blue) within a predetermined window of the captured scene for CS1 and CS2. The predetermined window of the captured scenes will correlate with the view each imaging device of each endoscopic camera system will be capturing at any instance in time. When two endoscopes have their imaging devices mostly pointed at the same area in the surgical field, the captured images for CS1 and CS2 will be in an area of greater overlapping lighting from the two endoscopes, and the illumination from each of the endoscope's illumination light source will influence to a greater extent the total quality, color, and degree of illumination picked up by each respective camera system CS1 and CS2. In contrast, when the two endoscopes have their imaging devices pointed in different directions, the area of overlapping lighting from the two endoscopes will be smaller, and the images captured by each separate camera systems CS1 or CS2 will be less influenced by lighting from the other camera system CS1 or CS2.

Figure 5:
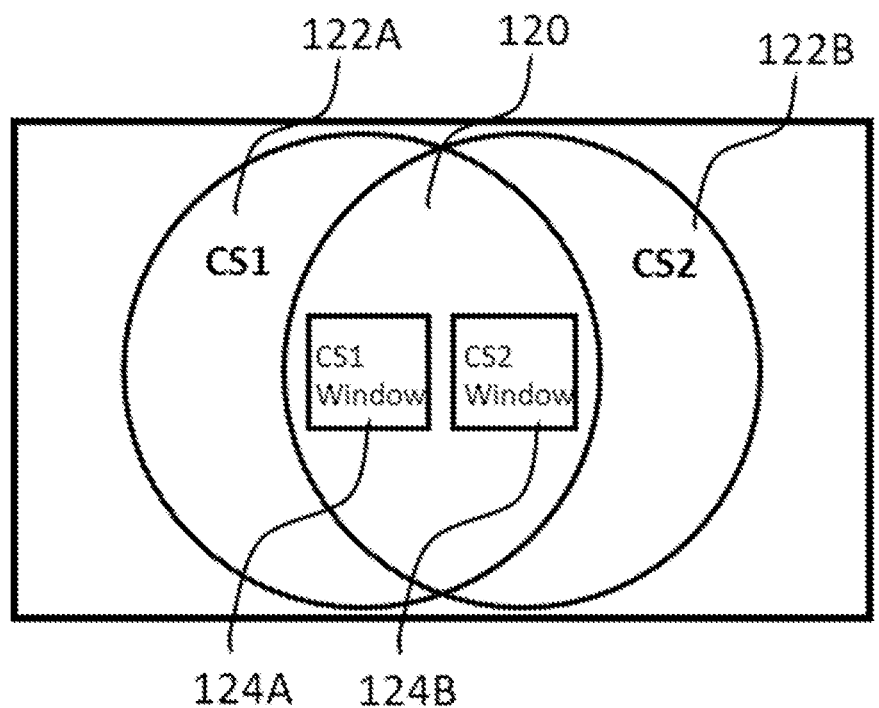
FIG. 5 is a diagrammatic drawing depicting the fields of view of two highly overlapping camera systems, with their respective color correction windows fully in the overlap area.

For example, as shown in diagrammatic FIG. 5, the endoscopes (CS1 and CS2) are pointed (mostly) at the same area in the surgical field, and the image frames captured by CS1 will be in a lighting overlap zone 120 of the light projection fields 122A and 122B from the respective light sources of CS1 and CS2. A small section of each image frame, namely CS1 window 124A for CS1, and CS2 window 124B for CS2 is the area in each camera system that samples light for white balancing purposes. In FIG. 5, CS1 window 124A and CS2 window 124B are completely in the lighting overlap zone 120. However, referring to diagrammatic FIG. 6, if the endoscopes (CS1 and CS2) are not pointed at the same area in the surgical field, the lighting overlap zone 120' of the light projection fields 122A' and 122B' from the respective light sources of CS1 and CS2 will be smaller, and the white balancing sections of the image frames captured by CS1 and CS2, as sampled by CS1 window 124A' and CS2 window 124B', respectively, will not be completely in the lighting overlap zone 120', in which case the images captured by each separate camera systems CS1 or CS2 and their white balancing sections CS1 window 124A' and CS2 window 124B' will be less influenced by lighting from the other camera system CS1 or CS2.

Figure 6:
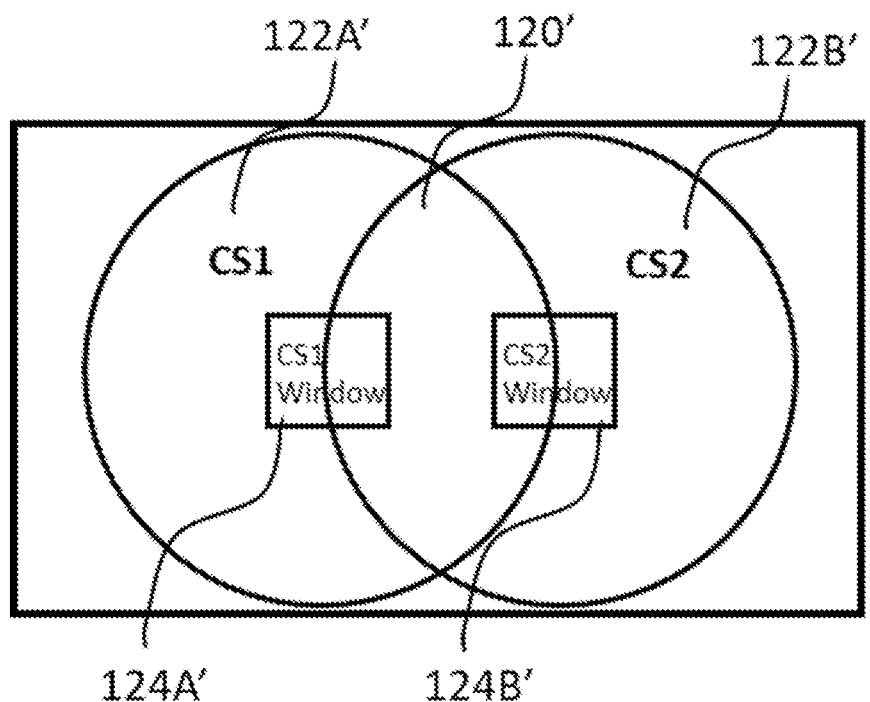
FIG. 6 is a diagrammatic drawing depicting the fields of view of two less overlapping camera systems, with their respective color correction windows only partially in the overlap area.

The predetermined windows CS1 window 124A/124A', and CS2 window 124B/124B' may be the usual exposure control or white balance windows. If each predetermined window is small, it is more likely to be in the overlapped area of the two camera images CS1 and CS2 and should yield a more appropriate color correction (See FIG. 5.) However, as shown in FIG. 6, if each window (CS1 window 124A' and CS2 window 124B') do not completely reside or are outside of the overlap area 120', the correction will be less effective, but nonetheless in the correct direction and can be used. Regardless of the degree of overlap, the average values of R, G, and B within a predetermined window of the captured scene for CS1 window and CS2 window are collected in memory, for example in the memory unit 62 of the color correction unit 24/46 as measurements SceneAB, for further processing.

In step 118, with only CS1 illumination switched on, the system measures the average values of R, G, and B within a predetermined window of the captured scene for CS1. These average values of R, G, and B are stored in the memory unit 62 in the color correction unit 24/46 as measurements SceneA, for further processing. The color correction unit 24/46 can control CS1 and CS2 to automatically accomplish the lighting states of CS1 and CS2.

In step 120, now with only CS2 illumination switched on, the system measures the average values of R, G, and B within a predetermined window of the captured scene for CS2. These average values of R, G, and B are stored in memory, for example as measurements SceneB, in the color correction unit 24/46, for further processing. The color correction unit 24/46 can control CS1 and CS2 to automatically accomplish the lighting states of CS1 and CS2.

Next, in step 122, a first comparison is carried out. If the detected SceneA measurements are significantly different as perceived through close observation from the detected SceneAB measurements, WB1' and CC1' are applied to the first camera system's CS1 digital signal processing path. Scene measurements can be taken for example by using the International Commission on Illumination (CIE) distance metric $\Delta E^*ab$ (also called $\Delta E^*$, or, inaccurately, $dE^*$, dE, or "Delta E") where delta is a Greek letter often used to denote difference, and E stands for Empfindung; German for "sensation". Alternative formulas include CIE76, CIE94, and CIEDE2000, and CMC 1:c (1984). See Backhaus, W.; Kliegl, R.; Werner, J. S. (1998). Color Vision: Perspectives from Different Disciplines. Walter de Gruyter. p. 188. ISBN 9783110154313; Valberg, A. (2005). Light Vision Color. Wiley. p. 278. ISBN 9780470849026; Sharma, Gaurav (2003). Digital Color Imaging Handbook (1.7.2 ed.). CRC Press. ISBN 0-8493-0900-X, and http://zschuessler.github-b.io/DeltaE/learn// However, whatever mathematical approach is taken, the inventors describe this herein as being "perceptible through close observation as significantly different."

Likewise, in step 124, a second comparison is carried out. If the detected SceneB measurements are significantly different as perceived through close observation from detected SceneAB measurements, WB2' and CC2' are applied to the second camera system's CS2 digital signal processing path.

In step 126, steps 122 and 124 are repeated as often as necessary to correct color balance using the formula below as CS1 and CS2 images change. As noted above, movement of either CS1 or CS2 could trigger operation of steps 114-126 or if the systems detected that white balance correction is needed at one predetermined interval between the steps, then the periodicity may be increased to ensure that the images being viewed are correctly white balanced.

The individual steps 118 and 120 with selected light sources turned off may last for a single video frame or as long as a few video frames. When one of the illumination sources is operating alone, such as CS1 illumination, the image from CS2, with its illumination momentarily off, may be dark. That is, the color correction steps may interrupt acceptable quality video frames from one or both imaging devices. In situations of this nature, a previous frame of CS1 video can be inserted until the CS1 light returns, as shown in optional step 128, and a previous frame of CS2 video can be inserted until the CS2 light returns, as shown in optional step 130. Previous saved frames should be substituted as needed to conceal missing or inferior frames.

The group of steps 112 (steps 114-130) can be initiated, for example, when an operator pushes the white balance reset and correction button 26, 38A, 38B, and/or 44 on the applicable Camera Control Unit 30A, 30B, 40 or color correction unit 24 or 46 or can be accomplished automatically and periodically when the endoscopes 10A and 10B are in use as described above.

The calculations to correct white balance gains for Red (R) are presented below. The calculations for Green (G) and Blue (B) follow the same formula and are set forth following the calculations for white balance gains for Red (R). As with other data utilized in the method, these formulas are saved, for example, in the memory unit 62 of the color correction unit 26/48. They can likewise reside in computer software on a general purpose computer, a Camera Control Unit, or can be included in one of the endoscopes.

Calculation to correct white balance gains for Red (R)

$R_{gain\ 1}$=initial red white balance gain for CS1
$R_{gain\ 2}$=initial red white balance gain for CS2
$R_{L1}$=Red value measured with CS1 illumination
$R_{L2}$=Red value measured with CS2 illumination
$R_{L1}+G_{L1}+B_{L1}$=sum of Red Green Blue values measured with CS1 illumination
$R_{L2}+G_{L2}+B_{L2}$=sum of Red Green Blue values measured with CS2 illumination
$R_{L1L2}$=Red value measured with CS1 and CS2 illumination
$R_{L1L2}+G_{L1L2}+B_{L1L2}$=sum of Red Green Blue values measured with CS1 and CS2 illumination $$R_{gain1\ corrected}=R_{gain1}\times[R_{L1}/(R_{L1}+G_{L1}+B_{L1})]/[R_{L1L2}/(R_{L1L2}+G_{L1L2}+B_{L1L2})] \quad \text{Equation 1R:}$$

$$R_{gain2\ corrected}=R_{gain2}\times[R_{L2}/(R_{L2}+G_{L2}+B_{L2})]/[R_{L1L2}/(R_{L1L2}+G_{L1L2}+B_{L1L2})] \quad \text{Equation 2R:}$$

Calculation to correct white balance gains for Green (G)

$G_{gain\ 1}$=initial green white balance gain for CS1
$G_{gain\ 2}$=initial green white balance gain for CS2
$G_{L1}$=Green value measured with CS1 illumination
$G_{L2}$=Green value measured with CS2 illumination
$R_{L1}+G_{L1}+G_{L1}$=sum of Red Green Blue values measured with CS1 illumination
$R_{L2}+G_{L2}+B_{L2}$=sum of Red Green Blue values measured with CS2 illumination
$G_{L1L2}$=Green value measured with CS1 and CS2 illumination
$R_{L1L2}+G_{L1L2}+B_{L1L2}$=sum of Red Green Blue values measured with CS1 and CS2 illumination $$G_{gain1\ corrected}=G_{gain1}\times[G_{L1}/(R_{L1}+G_{L1}+B_{L1})]/[G_{L1L2}/(R_{L1L2}+G_{L1L2}+B_{L1L2})] \quad \text{Equation 1G:}$$

$$G_{gain2\ corrected}=G_{gain2}\times[G_{L2}/(R_{L2}+G_{L2}+B_{L2})]/[G_{L1L2}/(R_{L1L2}+G_{L1L2}+B_{L1L2})] \quad \text{Equation 2G:}$$

Calculation to correct white balance gains for Blue (B)

$B_{gain\ 1}$=initial blue white balance gain for CS1
$B_{gain\ 2}$=initial blue white balance gain for CS2
$B_{L1}$=Blue value measured with CS1 illumination
$B_{L2}$=Blue value measured with CS2 illumination
$R_{L1}+G_{L1}+B_{L1}$=sum of Red Green Blue values measured with CS1 illumination
$R_{L2}+G_{L2}+B_{L2}$=sum of Red Green Blue values measured with CS2 illumination
$B_{L1L2}$=B1; value measured with CS1 and CS2 illumination
$R_{L1L2}+G_{L1L2}+B_{L1L2}$=sum of Red Green Blue values measured with CS1 and CS2 illumination $$B_{gain1\ corrected}=B_{gain1}\times[G_{L1}/(R_{L1}+G_{L1}+B_{L1})]/[B_{L1L2}/(R_{L1L2}+G_{L1L2}+B_{L1L2})] \quad \text{Equation 1B:}$$

$$B_{gain2\ corrected}=B_{gain2}\times[B_{L2}/(R_{L2}+G_{L2}+B_{L2})]/[B_{L1L2}/(R_{L1L2}+G_{L1L2}+B_{L1L2})] \quad \text{Equation 2B:}$$

In the above first equations for $R_{gain1\ corrected}$, $G_{gain1\ corrected}$, and $B_{gain1\ corrected}$, each of the numerators is the fraction of Red (or Green or Blue) in the measurement window with CS1 illumination. The denominator is the fraction of Red (or Green or Blue) in the measurement window with CS1 and CS2 illumination. The ratio of these measured Red fractions (or Green or Blue) is used to correct the Red white balance gain, the Green white balance gain, and the Blue white balance gain.

As noted above, the imaging devices in the individual endoscopes are linked to coordinate the timing of the steps noted to carry out the process. This can for example take place via a data link 36 through a color correction unit 24 to two camera control units A and B, as shown in FIG. 1, via a color correction unit 46 connected to camera control units AB, as shown in FIG. 2, and/or via a general purpose computer with software of the system connected to the camera control unit(s) and endoscopes or via a color correction unit inside a camera control unit.

The preferred embodiments of this invention have been disclosed, however, so that one of ordinary skill in the art would recognize that certain modifications would come within the scope of this invention.

What is claimed is:

1. A color correction system for at least two self-illuminated endoscopic camera systems, the color correction system comprising:
    a central processing unit;
    an input/output interface for camera control units; and
    a memory for retention of collected data and operating software or firmware for the color correction system;
    wherein each of the at least two self-illuminated endoscopic camera systems comprises an imaging device and an illumination source;
    wherein with the at least two self-illuminated endoscopic camera systems outside of a scene, the color correction system computes and saves white balancing information and color correction matrices for each of the at least two self-illuminated endoscopic camera systems, and the color correction system further computes and saves combined white balancing information and color correction matrices for the at least two self-illuminated endoscopic camera systems; and
    with the at least two self-illuminated endoscopic camera systems placed in a scene and with their illumination sources turned on, the color correction system measures and saves in the memory separate values of R (red), G (green), and B (blue) for each of at least two self-illuminated endoscopic camera systems as a combined scene measurement, and
    with the illumination source of one of the at least two endoscopic camera systems turned on and the illumination source of the other of the at least two endoscopic camera systems turned off, the color correction system measures and saves in the memory average values of R (red), G (green), and B (blue) for the endoscopic camera systems with the illumination source on, and repeating this measuring and saving step except with the illumination sources of the other of the at least two endoscopic camera systems switched from off to on and illumination source of the original endoscopic camera system switched from on to off,
    and carrying out comparisons of the scene measures of the at least two endoscopic camera systems when turned on against the combined scene measures and if necessary, making corrections to the white balance of the at least two endoscopic camera systems.

2. The color correction system of claim 1, wherein one of the at least two self-illuminated endoscopic camera systems can function as a master device and the other of the at least two self-illuminated endoscopic camera systems can function as a slave device.

3. The color correction system of claim 1, wherein illumination of either of the at least two self-illuminated endoscopic camera systems can be disabled or interleaved with frames of another of the at least two self-illuminated endoscopic camera systems.

4. The color correction system of claim 1, wherein camera control units in each of at least two self-illuminated endoscopic camera systems are connected via a data link to coordinate timing of the measuring steps.

5. The color correction system of claim 1, wherein at least two imaging devices and two illumination sources are connected to a single camera control unit.

6. The color correction system of claim 1, wherein the color correction system is a separate unit that interconnects to camera control units of each of the at least two self-illuminated endoscopic camera systems.

7. The color correction system of claim 1, wherein the color correction system comprises hardware, firmware, or software on a camera control unit of a first endoscopic camera system that interconnects to a second camera control unit of a second endoscopic camera system.

8. The color correction system of claim 1, wherein the color correction system comprises hardware, firmware, or software on at least one of the at least two self-illuminated endoscopic camera systems.

9. A device for color correction of at least two self-illuminated endoscopic camera systems, each self-illuminated endoscopic camera system having at least one imaging device, one illumination source, and a camera control unit, the device comprising:
  a central processing unit;
  an input/output interface for the camera control units;
  a memory for retention of collected data and operating software or firmware for the device for color correction; and
  a control to control operation of the color correction device; wherein when the color correction device is activated, white balancing of the at least two self-illuminated endoscopic camera systems takes place with the at least two self-illuminated endoscopic camera systems outside of a scene, and then with the two self-illuminated endoscopic camera systems placed in and used simultaneously in the scene, white balance correction of each of the at least two self-illuminated endoscopic camera systems will take place;
  wherein when the at least two self-illuminated endoscopic camera systems are outside of a scene, the color correction system carries out white balancing of the at least two self-illuminated camera systems to determine white balance gains for each of the at least two self-illuminated camera systems and the white balance gains are saved in the memory along with color correction matrices for each of the at least two self-illuminated camera systems; and
  based on each of the individual white balance gains and color correction matrices, the color correction system computes combined white balance gains and an accompanying set of combined color correction matrixes, and saves the combined white balance gains and the accompanying set of combined color correction matrixes in the memory;
  with the at least two self-illuminated endoscopic camera systems positioned in a scene, with illumination of the at least two endoscopic camera systems turned on, the color correction system separately measures average values of R (red), G (green), and B (blue) within a predetermined window of a captured scene for each of the at least two endoscopic camera systems and saves the average values in the memory as a combined scene measurements;
  with illumination of a first one of the at least two endoscopic camera systems turned on and the second of the at least two endoscopic camera systems turned off, the color correction system measures the average values of R, G, and B within the predetermined window of the captured scene for the one of the at least two endoscopic camera systems and saves average values of R, G, and B of the first one of the at least two endoscopic camera systems in the memory as a first scene measurements;
  with illumination of the second one of the at least two endoscopic camera systems turned on and the first one of the at least two endoscopic camera systems turned off, the color correction system measures the average values of R, G, and B within the predetermined window of the captured scene for the second one of the and saving average values of R, G, and B of the second one of the at least two endoscopic camera systems in the memory as a second scene measurements;
  the color correction system carries out a first comparison between the first scene measurements and the combined scene measurements, and if the first scene measurements is significantly different as perceived through close observation than the combined scene measurements, then applying the combined-light set of white balance gain and the color correction matrix to a digital signal processing path of the first one of the at least two endoscopic camera systems;
  the color correction system carries out a second comparison between the second scene measurements and the combined scene measurements, and if the second scene measurements is significantly different as perceived through close observation than the combined scene measurements, then the color correction system applies the combined-light set of white balance gain and the color correction matrix to a digital signal processing path of the second one of the at least two endoscopic camera systems; and
  the color correction system repeats the first and second comparisons as needed to correct the color balance of at least two self-illuminated endoscopic camera systems.

10. A method for color correction of at least two self-illuminated endoscopic camera systems, each self-illuminated endoscopic camera system having at least one imaging device and one illumination light, the method comprising the following steps:
  (A) with the at least two imaging device oriented outside of a scene;
  measuring and saving white balancing information and color correction matrices for each of the at least two self-illuminated endoscopic camera systems; and
  computing and saving combined white balancing information and color correction matrices for the at least two self-illuminated endoscopic camera systems; and
  (B) with the at least two imaging devices positioned in a scene;
  with the illumination sources turned on, measuring and saving in the memory separate values of R (red), G (green), and B (blue) for each of the at least two imaging devices as a combined scene;
  with the illumination source of one of the at least two endoscopic camera systems turned on and the illumination source of the other of the at least two endoscopic camera systems turned off measuring and saving in the memory average values of R (red), G (green), and B (blue) for the endoscopic camera systems with the illumination source on, and repeating this measuring and saving step except with the illumination source of the other of the least two endoscopic camera systems switched from off to on and the illumination source of the original endoscopic camera systems switched from on to off, and carrying out comparisons of the scene measurements of the at least two endoscopic camera systems when turned on against the combined scene measures and if necessary, making corrections to the white balance of the endoscopic camera systems.

11. The method for color correction of claim 10, further comprising repeating the steps of carrying out comparisons as needed to correct the color balance of at least two self-illuminated endoscopic camera systems.

12. The method for color correction of claim 10, wherein the at least two self-illuminated endoscopic camera systems each comprise a camera control unit and the camera control units are connected via a data link to coordinate timing of the measuring steps.

13. The method for color correction of claim 10, wherein the color correction system comprises hardware, firmware, or software on at least one camera control unit.

14. A method for color correction of at least two self-illuminated endoscopic camera systems, each self-illuminated endoscopic camera system having an imaging device, an illumination light, and a camera control unit, the method comprising the following steps:

with the at least imaging devices oriented outside of a scene;
(a) white balancing the at least two self-illuminated camera systems to determine white balance gains for each of the at least two self-illuminated camera systems and saving the white balance gains in a memory along with color correction matrices for each of the at least two self-illuminated camera systems; and
(b) based on each of the individual white balance gains and color correction matrices, computing combined white balance gains and an accompanying set of combined color correction matrices, and saving the combined white balance gains and the accompanying set of combined color correction matrices in the memory; and
with the at least two imaging devices positioned in a scene;
(c) with illumination of the at least two endoscopic camera systems turned on, separately measure average values of R (red), G (green), and B (blue) within a predetermined window of a captured scene for each of the at least two endoscopic camera systems and save in memory as a combined scene measurements;
(d) with illumination of a first one of the at least two endoscopic camera systems turned on and the second of the at least two endoscopic camera systems turned off, measuring the average values of R, G, and B within the predetermined window of the captured scene for the one of the at least two endoscopic camera systems and saving average values of R, G, and B of the first one of the at least two endoscopic camera systems in memory as a first scene measurements;
(e) with illumination of the second one of the at least two endoscopic camera systems turned on and the first one of the at least two endoscopic camera systems turned off, measuring the average values of R, G, and B within the predetermined window of the captured scene for the second one of the at least two endoscopic camera systems and saving average values of R, G, and B of the second one of the at least two endoscopic camera systems in memory as a second scene measurements;
(f) carrying out a first comparison between the first scene measurements and the combined scene measurements, and if the first scene measurements is significantly different as perceived through close observation than the combined scene measurements, then applying the combined-light set of white balance gain and the color correction matrix to a digital signal processing path of the first one of the at least two endoscopic camera systems;
(g) carrying out a second comparison between the second scene measurements and the combined scene measurements, and if the second scene measurements is significantly different as perceived through close observation than the combined scene measurements, then applying the combined-light set of white balance gain and the color correction matrix to a digital signal processing path of the second one of the at least two endoscopic camera systems; and
(h) repeating steps (f) and (g) as needed to correct the color balance of at least two self-illuminated endoscopic camera systems.

15. The method for color correction of at least two self-illuminated endoscopic camera systems of claim 14, wherein if video quality from one of the at least two self-illuminated endoscopic camera systems is not acceptable due to missing video frames during a time when one of at least two endoscopic camera systems is turned off, then inserting previous video frames from that one of the at least two endoscopic camera systems to replace the missing video frames.

* * * * *